US008232067B2

(12) United States Patent
Blumberg et al.

(10) Patent No.: US 8,232,067 B2
(45) Date of Patent: Jul. 31, 2012

(54) DISRUPTING FCRN-ALBUMIN INTERACTIONS

(75) Inventors: Richard S. Blumberg, Waltham, MA (US); Timothy T. C. Kuo, Chestnut Hill, MA (US)

(73) Assignee: Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/322,983

(22) PCT Filed: May 28, 2010

(86) PCT No.: PCT/US2010/036572
§ 371 (c)(1),
(2), (4) Date: Jan. 11, 2012

(87) PCT Pub. No.: WO2010/138814
PCT Pub. Date: Dec. 2, 2010

(65) Prior Publication Data
US 2012/0107845 A1    May 3, 2012

Related U.S. Application Data

(60) Provisional application No. 61/182,479, filed on May 29, 2009.

(51) Int. Cl.
*G01N 31/00* (2006.01)
*G01N 33/53* (2006.01)
(52) U.S. Cl. ........ 435/7.21; 435/7.1; 436/501; 436/518; 424/9.1; 424/520; 422/50; 530/300; 530/350
(58) Field of Classification Search ........................ None
See application file for complete search history.

(56) References Cited

U.S. PATENT DOCUMENTS

| 2005/0037947 A1 | 2/2005 | Bitonti et al. |
| 2007/0003549 A1 | 1/2007 | Ignatovich et al. |

FOREIGN PATENT DOCUMENTS
WO    2006/118772    11/2006

OTHER PUBLICATIONS

Andersen et al., "FcRn binding properties of an abnormal truncated analbuminemic albumin variant," Clin. Biochem., 43(4-5):367-372 (2010—Epub Dec. 16, 2009).
Anderson et al., "A strategy for bacterial production of a soluble functional human neonatal Fc receptor," J. Im. Methods, 331(1-2):39-49 (2008).
Bhattacharya et al., "Crystallographic analysis reveals common modes of binding of medium and long-chain fatty acids to human serum albumin," J. Mol. Biol., 303:721 (2000).
Blome and Schengrund, "Multivalent binding of ricin to bovine serum albumin-based neoglycoconjugates," Toxicon. 51(7):1214-1224 (2008).
Chaudhury et al., "Albumin Binding to FcRn: Distint from the FcRn-IgG Interaction," Biochemistry, 45:4983-4990 (2006).
Damsten et al., "Liquid chromatography/tandem mass spectrometry detection of covalent binding of acetaminophen to human serum albumin," Drug Metabl. Dispos., 35(8):1408-1417 (2007).
International Search Report issued in PCT/US2010/036572 on Feb. 18, 2011.
Qiao et al., "Dependence of antibody-mediated presentation of antigen on FcRn," Proc. Natl. Acad. Sci. USA, 105(27):9337-9342 (2008).
Roopenian et al., "FcRn: the neonatal Fc receptor comes of age," Nat. Rev. Immunol., 7(9):715-725 (Epub. 2007).
Varshney et al., Ligand binding strategies of human serum albumin: How can the cargo be optimized, Chirality, 22:77-87 (2010—Epub Mar. 24, 2009).
Zeuzam et al., "Albinterferon alfa-2b dosed every two or four weeks in interferon-naïve patients with genotype 1 chronic hepatitis C," Hepatology, 48:407-417 (2008).

*Primary Examiner* — Lisa Cook
(74) *Attorney, Agent, or Firm* — Fish & Richardson P.C.

(57) ABSTRACT

Provided herein are, inter alia, methods for identifying a candidate compound for treating the toxic effects of compounds or molecules that bind to albumin in a subject. The methods include identifying test compounds that inhibit the binding between FcRn and albumin.

19 Claims, 6 Drawing Sheets

_US 8,232,067 B2_

DISRUPTING FCRN-ALBUMIN INTERACTIONS

CLAIM OF PRIORITY

This application is a 371 application of International Application No. PCT/US2010/036572, filed on May 28, 2010, and claims priority under 35 USC §119(e) to U.S. Patent Application Ser. No. 61/182,479, filed on May 29, 2009, the entire contents of which are hereby incorporated by reference.

FEDERALLY SPONSORED RESEARCH OR DEVELOPMENT

This invention was made with Government support under Grant Nos. NIH RO1 DK53056 and NIH K08 DK071798 awarded by the National Institutes of Health. The Government has certain rights in the invention.

TECHNICAL FIELD

Provided herein are methods for identifying a candidate compound for treating the toxic effects of compounds or molecules that bind to albumin in a subject, and methods for treating subjects who have ingested or been exposed to a toxin.

BACKGROUND

The neonatal Fc receptor (FcRn) is a MHC class I-like molecule that is known to bind IgG at acidic, but not basic pH. As such, FcRn protects IgG from degradation, mediates the bidirectional transport of IgG and IgG/antigen complexes across polarized epithelial cells, and functions in IgG-dependent antigen presentation within dendritic cells. FcRn has also been found to bind albumin in a manner that does not overlap with its binding to IgG, and similarly protects albumin from degradation (Chaudhury et al., Biochemistry 2006, 45:4983-4990).

SUMMARY

Provided herein are methods of identifying compounds that disrupt an interaction (e.g., binding) between an FcRn polypeptide and an albumin polypeptide. In some embodiments, methods for identifying compounds that disrupt an FcRn-Albumin interaction (e.g., binding) are provided. In some embodiments, methods for identifying variant albumin polypeptides that are unable to interact with (e.g., bind to) an FcRn polypeptide are provided.

In one aspect, provided herein are methods of identifying a candidate compound for decreasing the concentration of an albumin-binding toxin in a subject. The methods include contacting (a) a test compound, (b) an FcRn polypeptide or albumin-binding fragment thereof, and (c) an albumin polypeptide or FcRn-binding fragment thereof, under conditions and for a time sufficient to allow binding between the FcRn polypeptide or fragment thereof and the albumin polypeptide or fragment thereof; and detecting whether the test compound inhibits binding between the FcRn polypeptide or fragment thereof and the albumin polypeptide or fragment thereof; wherein a test compound that inhibits binding between the FcRn polypeptide or fragment thereof and the albumin polypeptide or fragment thereof is a candidate compound for decreasing the concentration of an albumin-binding toxin in a subject.

In some embodiments, the test compound is selected from the group consisting of: a polypeptide, a small molecule, a nucleic acid, an antibody, an antibody fragment, and combinations thereof. The albumin polypeptide used in the methods can be a wild type albumin polypeptide or a human albumin polypeptide. The FcRn polypeptide can be a wild type FcRn polypeptide or a human FcRn polypeptide. In some embodiments, either one or both of the FcRn polypeptide or fragment thereof and the albumin polypeptide or fragment thereof are fluorescently labeled.

In some embodiments, the methods further include selecting a test compound that inhibits binding between the FcRn polypeptide or fragment thereof and the albumin polypeptide or fragment thereof, administering the test compound to a subject, e.g., a patient or test animal, expressing an FcRn polypeptide or albumin-binding fragment thereof and an albumin polypeptide or FcRn-binding fragment thereof; and determining a level of the albumin polypeptide or fragment thereof in a body fluid of the subject, e.g., test animal; wherein a change in the level of the albumin polypeptide or fragment thereof in the body fluid of the subject or animal in the presence of the test compound as compared to in the absence of the test compound indicates that the test compound is a candidate compound for decreasing the concentration of an albumin-binding toxin in a subject. The body fluid tested can be selected from the group consisting of bile, urine, and feces, and wherein the change in the level of the albumin polypeptide or fragment thereof is an increase in the level in the body fluid. The body fluid test can also be blood or lymph, and wherein the change in the level of the albumin polypeptide or fragment thereof is a decrease in the level in the blood or lymph.

In some embodiments, the methods can also include selecting a test compound that inhibits binding between the FcRn polypeptide or fragment thereof and the albumin polypeptide or fragment thereof; administering the test compound and an albumin-binding toxin to a test animal expressing an FcRn polypeptide or albumin-binding fragment thereof and an albumin polypeptide or FcRn-binding fragment thereof; and determining an effect of the albumin-binding toxin in the test animal; wherein a change in the effect of the albumin-binding toxin in the presence of the test compound as compared to in the absence of the test compound indicates that the test compound is a candidate compound for decreasing the concentration of the albumin-binding toxin in a subject. The step of administering is selected from the group consisting of: intravenous administration, intradermal administration, subcutaneous administration, oral administration, transdermal administration, transmucosal administration, rectal administration, and combinations thereof.

In one aspect, described herein are methods for treating a disorder associated with an albumin-binding toxin (e.g., by decreasing the concentration of the albumin-binding toxin) in a subject (e.g., in the blood of a subject) by identifying a subject in need of such treatment, and administering to the subject a compound, e.g., one or both of (i) a variant of albumin that binds the toxin but does not bind FcRn, or (ii) an antibody, a polypeptide, or a small molecule, that blocks the binding between albumin and FcRn. In some embodiments, the compound is an anti-FcRn antibody, e.g., the ADM31 antibody described in Qiao et al., Proc Natl Acad Sci USA. 105(27):9337-42 (2008), or a variant (e.g., chimeric or humanized) or antigen-binding portion thereof. In some embodiments, the compound is an anti-albumin antibody, e.g., the A6684 antibody available from SIGMA-ALDRICH (St. Louis, Mo.), or a variant (e.g., chimeric or humanized) or antigen-binding portion thereof.

In another aspect, methods for identifying variant albumin polypeptides that are deficient in binding an FcRn polypeptide, but retains its ability to bind albumin-binding compounds or molecule, are disclosed. In some embodiments, such methods include contacting an FcRn polypeptide, e.g., a wild-type FcRn, with a variant albumin polypeptide, and determining the binding of the variant albumin polypeptide to the FcRn polypeptide. A decrease in binding between the FcRn polypeptide and the variant albumin polypeptide compared to binding that would occur between the FcRn polypeptide and a reference (e.g., wild type) albumin polypeptide indicates that the variant albumin polypeptide is deficient in binding the FcRn polypeptide. In some embodiments, the reference albumin polypeptide is a wild type albumin polypeptide. In some embodiments, the reference albumin polypeptide is a human albumin polypeptide. In some embodiments, the reference FcRn polypeptide is a wild type FcRn polypeptide. In some embodiments, the reference FcRn polypeptide is a human FcRn polypeptide. In some embodiments, the FcRn polypeptide is expressed on the surface of a cell.

In some embodiments, methods of identifying a variant albumin polypeptide that is deficient in binding an FcRn polypeptide can include administering the variant albumin polypeptide to an animal expressing the FcRn polypeptide, and determining the level of the variant albumin polypeptide in a body fluid of the animal, wherein a difference in the level of variant albumin polypeptide in the body fluid of the animal compared to the level of a reference albumin polypeptide that would be present in the body fluid of the animal indicates that the variant albumin polypeptide is deficient in binding the FcRn polypeptide. In some embodiments, the body fluid is bile, urine, or feces, and an increase in the level of albumin polypeptide present in the bile, urine, or feces indicates that the variant albumin polypeptide is deficient in binding the FcRn polypeptide. In some embodiments, the body fluid is blood or lymph, and a decrease in the level of albumin polypeptide present in the blood or lymph indicates that the variant albumin polypeptide is deficient in binding the FcRn polypeptide. In some embodiments, the reference albumin polypeptide is a wild type albumin polypeptide. In some embodiments, the reference albumin polypeptide is a human albumin polypeptide. In some embodiments, the animal expresses a wild type FcRn polypeptide. In some embodiments, the animal expresses a human FcRn polypeptide. In some embodiments, the animal is contacted with the variant albumin polypeptide by intravenous administration, intradermal administration, subcutaneous administration, oral administration, transdermal administration, transmucosal administration, and/or rectal administration.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
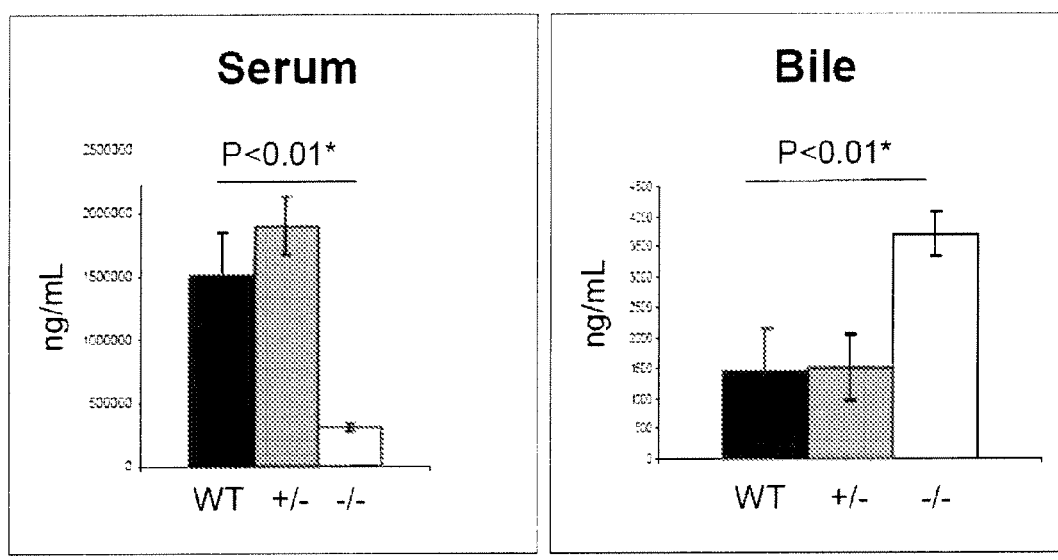
FIG. 1 is a pair of bar graphs showing elevated levels of mouse IgG in the bile of FcRn deficient (−/−) mice despite low levels in blood.

Provided herein are, inter alia, methods of identifying compounds that disrupt an interaction, e.g., binding, between an FcRn polypeptide and an albumin polypeptide. In some embodiments, methods for identifying a compound that disrupts and FcRn-Albumin interaction are provided. In some embodiments, methods for identifying a variant albumin polypeptide that is unable to interact with an FcRn polypeptide are provided. Also provided are methods for treating disorders or effects associated with compounds that bind albumin.

Efforts to date related to the FcRn-albumin interaction have been directed to exploiting the FcRn-albumin interaction in order to extend the half-life of therapeutic albumin cargo conjugates. For example, Albuferon is an albumin-interferon conjugate sold by Human Genome Sciences. By coupling interferon to albumin, the half-life of the interferon moiety is extended by virtue of albumin's interaction with FcRn, thus providing an improved treatment option for chronic hepatitis C (see e.g., Zeuzam et al. Hepatology 2008; 48:407-417, incorporated herein by reference in its entirety). Another example of an albumin conjugate is Abraxane, albumin conjugated to paclitaxel, which is made by BMS, for the treatment of lung, ovarian, and breast cancer.

The present inventors have discovered that in the absence of FcRn expression in mice, albumin is lost into the bile from the circulation, confirming a scavenging role of FcRn in the biliary system. Mice lacking FcRn expression also lose exogenous injected albumin into the bile from the circulation. The present disclosure encompasses the discovery that disrupting the FcRn-albumin interaction will lead to loss of albumin to the bile, urine, or feces from the circulation and subsequent excretion from the body, along with any other molecule which is bound to the albumin. Albumin is known to bind a wide range of compounds and molecules, for example, copper, hematin, long-chain fatty acid, zinc, bilirubin, thyroxine, eicosanoids, tryptophan, vitamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, and quinidine (see, e.g., Varshney et al., Ligand binding strategies of human serum albumin: How can the cargo be optimized. Chirality. 2010(22):77-87). Ricin is also known to bind to albumin (Blome and Schengrund., Toxicon. 2008 51(7):1214-24). Also, acetaminophen has been found to bind human serum albumin (Damsten et al., Drug Metab Dispos. 2007 35(8):1408-17). Excretion of such compounds and molecules would be advantageous in the treatment of various conditions including, without limitation, toxic overdoses of a variety of drugs (e.g., albumin conjugated medications and fusion proteins), heavy metal toxicity, bacterial overload, bacterial sepsis, and a variety of other conditions. Thus, identification of compounds that disrupt the binding between FcRn and albumin, as well as identification of albumin variants that are deficient in binding FcRn, is desirable since administration of such compounds or albumin variants to a subject (e.g., a human or animal) could mediate excretion of toxic compounds from the circulation Any of the various screening methods disclosed herein will be useful in identifying compounds or albumin variants that disrupt the FcRn-albumin interaction. Such compounds can be administered to a host, leading to loss of albumin and any other molecule bound to albumin. In cases in which a molecule bound to albumin is a toxic molecule, compounds and albumin variants identified by one or more methods disclosed herein can be used to "detoxify" the host.

FcRn

The terms "FcRn" and "FcRn polypeptide" as used herein refer to the neonatal Fc receptor polypeptide. FcRn is found on the cell surface and is responsible for the transport of immunoglobulin from the mother to the neonate. In some animals, e.g., rats, mice and ruminants, FcRn is expressed in the gut of the newborn and transports IgG from the colostrum to the blood during the first 24 hours of life. In humans, FcRn transports IgG across the placenta. FcRn also plays a role in maintaining the long plasma half-life of IgG and albumin. The FcRn polypeptide includes an alpha chain that is homologous to MHC class-I molecules, the alpha chain being associated with beta-2-microglobulin. The receptor binds to the interface between the CH2 and CH3 domains of the IgG heavy chains in the Fc of the IgG molecule.

In some embodiments, an FcRn polypeptide used in one or more screening methods described herein is a wild type FcRn polypeptide. Wild type FcRn polypeptides are known in the art. See e.g., Roopenian et al, Nat Rev Immunol; 7(9):715-25. Epub 2007, incorporated herein by reference in its entirety. Exemplary FcRn nucleic acids and polypeptides that can be used in one or more of the screening methods described herein are those described by Genbank sequence identifiers NM_001136019.2 (nucleic acid) and NP_001129491.1 (protein). In some embodiments, an FcRn polypeptide used in one or more screening methods described herein is a non-wild type FcRn polypeptide. For example, an FcRn polypeptide used as described herein may be engineered to include one or more amino acid changes as compared to a wild type FcRn polypeptide. As will be recognized by those of ordinary skill in the art, in order to screen for compounds or albumin variants that disrupt binding between FcRn and albumin, a non-wild type FcRn polypeptide used in accordance with one or more methods described herein should retain the ability to at least partially bind albumin.

It has been shown that the conserved H166 residue in the human FcRn is critical for albumin binding (Andersen et al., Eur. J. Immunol. 2006. 36: 3044-3051). Those of ordinary skill in the art will be able to engineer specific amino acid alterations in a wild type FcRn using standard molecular biology protocols to suit their experimental needs (see e.g., Sambrook, Fritsch & Maniatis, Molecular Cloning: A Laboratory Manual, 2nd Ed., Cold Spring Harbor Press N.Y., 1989). Anti-FcRn antibodies that specifically block the interaction between FcRn and albumin can also be generated by methods known in the art and described herein.

In some embodiments, an FcRn polypeptide used in one or more screening methods described herein is a human FcRn polypeptide. In some embodiments, an FcRn polypeptide used in one or more screening methods described herein is a wild type human FcRn polypeptide. Alternatively, a human FcRn polypeptide may be engineered as described above to include one or more amino acid changes as compared to a wild type human FcRn polypeptide. In some embodiments, an FcRn polypeptide used in one or more screening methods described herein is a non-human FcRn polypeptide. Examples of non-human FcRn polypeptides that may be used in methods described herein include, without limitation, mouse FcRn, rat FcRn, porcine FcRn, cow FcRn, and the like.

Albumin

The terms "albumin" and "albumin polypeptide" as used herein refer to serum albumin polypeptides. Albumin is produced in the liver and is the most abundant blood plasma protein. Albumin polypeptides are important in regulating blood volume by maintaining appropriate colloid osmotic pressure. Human serum albumin is a monomer of 585 amino acid residues, and includes three homologous a-helical domains: domain I, domain II and domain III. Each domain contains 10 helices and is divided into antiparallel six-helix and four-helix subdomains. Deletion studies suggest that domain III alone is sufficient for binding to FcRn (Chaudhury et al., Biochemistry 2006, 45:4983-4990). A truncated human albumin that does not bind FcRn and has a low serum level has been identified (Andersen et al., Clin Biochem., 2010, 43(4-5):367-72. Epub 2009 Dec. 16).

Albumin is known to bind and carry a wide variety of small molecules, including lipid soluble hormones, bile salts, unconjugated bilirubin, fatty acids, calcium, ions, transferrin, hemin, and tryptophan. Albumin also binds various drugs such as warfarin, phenobutazone, clofibrate and phenytoin, and its binding can alter the drugs' pharmacokinetic properties. See e.g., Varshney et al., "Ligand binding strategies of human serum albumin: How can the cargo be utilized?", published electronically in Chirality, Mar. 24, 2009, incorporated by reference in its entirety. Competition between drugs for albumin binding sites may cause drug interaction by increasing the free fraction of one of the drugs, thus affecting the drugs' effective potency. A crystallographic study of five albumin-fatty acid complexes identified a total of seven binding sites that are occupied by all medium-chain and long-chain fatty acids, and four additional sites occupied by medium-chain fatty acids (Bhattacharya et al., 2000, J. Mol. Biol. 303:721).

The term "albumin-binding toxin" refers to a compound, drug, or molecule that binds albumin. While it may be desirable under some circumstances to decrease the concentration of an albumin-binding toxin in a subject, the term is not limited to a compound, drug, or molecule that is labeled as a "toxin." Albumin-binding toxins can include, for example, copper, hematin, long-chain fatty acid, zinc, bilirubin, thyroxine, eicosanoids, tryptophan, citamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, quinidine, Ricin, and acetaminophen.

In some embodiments, an albumin polypeptide used in one or more screening methods described herein is a wild type albumin polypeptide. Wild type albumin polypeptides are known in the art. Exemplary albumin polypeptides that can be used in one or more screening methods described herein are those described by Genbank sequence identifier NP_000468.1 (human), NP_033784.2 (mouse) and NP_599153.2 (rat). In some embodiments, an albumin polypeptide used in one or more screening methods described herein is a non-wild type albumin polypeptide. For example, an albumin polypeptide used as described herein may be engineered to include one or more amino acid changes as compared to a wild type albumin polypeptide. In some cases, a non-wild type albumin polypeptide used in accordance with one or more methods described herein retains the ability to at least partially bind FcRn. Those of ordinary skill in the art will be able to engineer specific amino acid alterations in a wild type albumin using standard molecular biology protocols to suit their experimental needs (see e.g., Sambrook et al., Fritsch & Maniatis, *Molecular Cloning: A Laboratory Manual,* 2nd Ed., Cold Spring Harbor Press N.Y., 1989).

In some embodiments, an albumin polypeptide used in one or more screening methods described herein is a human albumin polypeptide. In some embodiments, an albumin polypeptide used in one or more screening methods described herein is a wild type human albumin polypeptide. Alternatively, a human albumin polypeptide may be engineered as described above to include one or more amino acid changes as compared to a wild type human albumin polypeptide. In some embodiments, an albumin polypeptide used in one or more screening methods described herein is a non-human albumin polypeptide. Examples of non-human albumin polypeptides that may be used in methods described herein include, without limitation, mouse albumin, rat albumin, porcine albumin, cow albumin, and the like.

Identification of Compounds That Disrupt Binding Between FcRn and Albumin

In some embodiments, methods of identifying compounds that disrupt an interaction between an FcRn polypeptide and an albumin polypeptide are disclosed. In some embodiments, such methods include contacting the FcRn polypeptide with the compound and the albumin polypeptide to generate a test sample and determining the binding of the albumin polypeptide to the FcRn polypeptide in the test sample, wherein a decrease in binding between the FcRn polypeptide and the albumin polypeptide in the test sample compared to binding that would occur between the FcRn polypeptide and the albumin polypeptide in a sample lacking the compound indicates that the compound disrupts the interaction between the FcRn polypeptide and the albumin polypeptide. In some embodiments, a test compound can be a polypeptide, a small molecule, a nucleic acid, an antibody, and/or an antibody fragment. In some embodiments, the albumin polypeptide is a wild type albumin polypeptide. In some embodiments, the albumin polypeptide is a wild type albumin polypeptide. In some embodiments, the FcRn polypeptide is a wild type FcRn polypeptide. In some embodiments, the FcRn polypeptide is a wild type FcRn polypeptide. In some embodiments, the FcRn polypeptide is expressed on the surface of a cell.

Any of a variety of methods to detect disruption of binding between FcRn and albumin may be used. For example, fluorescence resonance energy transfer ("FRET") methods may be used. FRET occurs when an excited donor fluorophore transfers its energy to an acceptor fluorophore in close proximity. Thus, if a first molecule (e.g., FcRn) and a second molecule (e.g. albumin) are suspected of binding, the first molecule can be tagged with a first fluorescent label that upon excitation emits radiation of a given wavelength. If the second molecule is labeled with a second fluorescent label, which second fluorescent label is excited by the emission radiation of the first label, binding of the first and second molecules can be detected or measured by exciting the first molecule containing the first label, and detecting or measuring emission radiation of the second molecule containing the second label. In some embodiments, the first and second labels are excited by different wavelengths. In such embodiments, excitation of the first label will be expected to have little or no direct effect on excitation of the second label. In some embodiments, the excitation wavelengths of the first and second labels overlap. In such embodiments, excitation of the first label will also directly excite the second label to at least some extent. Thus, in detecting or measuring binding, the emission of the second label will need to be corrected for the additional excitation. A compound that disrupts binding between FcRn and albumin will be expected to result in a decrease in the emission radiation of the second label.

In some embodiments, disruption of binding between FcRn and albumin can be detected by chromatographic methods. For example, after incubating FcRn and albumin in a test sample in the presence or absence of a test compound, the FcRn or the albumin may be isolated from the test sample. Isolation may be performed by any of a variety of techniques including, without limitation, column chromatography, antibody pull-downs, fractionation, etc. If FcRn and albumin bind, isolation of one polypeptide will result in isolation of the other. Standard chromatographic methods known to those skilled in the art may be used. In some embodiments, the FcRn, the albumin or both can be labeled (e.g. with a radioactive or non-radioactive label) to facilitate detection of the polypeptide after isolation. In some embodiments, neither polypeptide is labeled, and the polypeptides are detected by standard techniques such as, without limitation, Western blotting, mass spectrometry, and antibody staining.

In some cases, the protein-protein interaction is detected by reconstituting domains of an enzyme, e.g., beta-galactosidase (see Rossi et al, *Proc. Natl. Acad. Sci. USA*, 94:8405-8410 (1997)).

In some embodiments, the protein-protein interaction is assessed by fluorescence ratio imaging (Bacskai et al, *Science,* 260:222-226 (1993)) of suitable chimeric constructs of a first and second protein, or by variants of the two-hybrid assay (Fearon et al, *Proc. Nat'l. Acad. Sci USA,* 89:7958-7962 (1992); Takacs et al, *Proc. Natl. Acad. Sci. USA,* 90:10375-10379 (1993); Vidal et al, *Proc. Nat'l. Acad. Sci. USA,* 93:10315-10320 (1996); Vidal et al, *Proc. Nat'l Acad. Sci USA,* 93:10321-10326 (1996)) employing suitable constructs of first and second protein tailored for a high throughput assay to detect compounds that inhibit the first protein/second protein interaction. These embodiments have the advantage that the cell permeability of compounds that act as modulators in the assay is assured.

Mezo et al. (PNAS, 2008, 105(7): 2337-2342) describes a phage display screen to identify peptides that interfere with the interaction between FcRn and IgG, and various methods for assaying the ability of test peptides to block the interaction. Those of ordinary skill in the art would be able to design similar screens to identify peptides that block the binding between FcRn and albumin.

In some embodiments, disrupted binding between FcRn and albumin caused by a compound can be expressed as percentage of the binding that would occur in the absence of the compound. For example, a compound can disrupt binding between FcRn and albumin by at least 10%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, or more. In some embodiments, a compound can disrupt binding between FcRn and albumin by at least 50%, e.g., least 50%, at least 55%, at least 60%, at least 65%, at least 70%, at least 75%, at least 80%, at least 85%, at least 90%, or more. In some embodiments, a compound can disrupt binding between FcRn and albumin by at least 90%, e.g., least 90%, at least 91%, at least 92%, at least 93%, at least 94%, at least 95%, at least 96%, at least 97%, at least 98%, at least 99%, or more. In general, the more a compound disrupts FcRn binding to albumin, the greater its utility as a therapeutic. In some cases, however, it will be desirable to identify a compound that disrupts FcRn binding to albumin only to a certain maximal percent. Those of ordinary skill in the art will be aware of such cases, and will be able to use methods described herein to identify such a compound.

Test Compounds

Various test compounds can be screened by one or more methods described herein. Test compounds can include, without limitation, polypeptides, small molecules, nucleic acids, antibodies, and/or antibody fragments. In some embodiments, a single test compound is screened according to one or more methods described herein. In some embodiments, a combination of two or more compounds is screened according to one or more methods described herein.

Test compounds that are identified as disrupting the interaction between FcRn and albumin can be considered a candidate compound for therapeutic uses. A candidate compound that has been screened in an in vitro model (e.g., a cell expressing an FcRn polypeptide on its surface) and/or an in vivo model (e.g., a mouse model) and determined to disrupting the interaction between FcRn and albumin can be considered a candidate therapeutic agent. Candidate therapeutic agents, once successfully screened in a clinical setting, are therapeutic agents. Candidate therapeutic agents and therapeutic agents can be optionally optimized and/or derivatized, and formulated with physiologically acceptable excipients to form pharmaceutical compositions.

In some embodiments, a compound to be screened according to one or more methods described herein is a polypeptide. Polypeptides to be screened can be naturally occurring polypeptides. Alternatively, polypeptides to be screened according to one or more methods described herein can be non-naturally occurring polypeptides, e.g., engineered by the hand of man. In some embodiments, polypeptides to be screened can contain both naturally occurring and non-naturally occurring moieties. For example, a naturally occurring polypeptide can be fused with a non-naturally occurring polypeptide, which fusion polypeptide can be screened by one or more methods described herein. As an additional example, one or more amino acid residues of a naturally occurring polypeptide can be altered, such that the engineered polypeptide differs from the naturally occurring polypeptide at one or more positions. In some embodiments, one or more amino acid residues of a naturally occurring polypeptide are altered to generate an engineered polypeptide such that the engineered polypeptide is at least 50%, e.g., 50%, 55%, 60%, 65%, 70%, 75%, 80%, 85%, 90%, 95%, 96%, 97%, 98%, 99% or higher, identical to the naturally occurring polypeptide. As will be understood by those of ordinary skill in the art, polypeptides can be chemically modified (e.g., glycosylated, pegylated, etc.). Such modified polypeptides can also be screened by one or more methods described herein. Polypeptides to be screened according to one or more methods described herein can be of any length. In some embodiments, polypeptides to be screened will be less that about 500 amino acid residues in length, e.g., less than about 500, less than about 400, less than about 300, less than about 200, less than about 100, less than about 90, less than about 80, less than about 70, less than about 60, less than about 50, less than about 40, less than about 30, less than about 20, less than about 10, less than about 5, or fewer amino acid residues in length. In some embodiments, polypeptides to be screened will be at least 5 amino acid residues in length, e.g., at least 5, at least 10, at least 20, at least 30, at least 40, at least 50, at least 60, at least 70, at least 80, at least 90, at least 100, at least 200, at least 300, at least 400, at least 500, or more amino acid residues in length.

In some embodiments, a compound to be screened according to one or more methods described herein is a small molecule. As used herein, "small molecules" refers to small organic or inorganic molecules of that is not a polymer. In general, small molecules to be screened according to methods described herein will have a molecular weight of less than 3,000 Daltons (Da), although small molecules that can be screened by the presently disclosed methods are not limited to such a maximal weight. In some embodiments, small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

Small molecules to be screened according to one or more methods described herein may be naturally occurring or may be synthetic in origin. In some embodiments, small molecules to be screened can be generated via combinatorial chemistry. For example, small molecules to be screened can be part of a combinatorial chemistry library. Libraries screened using the methods disclosed herein can comprise a variety of types of test compounds. A given library can comprise a set of structurally related or unrelated test compounds. A set of diverse molecules can be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6, 1997, incorporated by reference in its entirety). Additionally or alternatively, a number of small molecule libraries are commercially available. Exemplary small molecule test compounds are listed in U.S. Pat. No. 6,503,713, incorporated herein by reference in its entirety.

In some embodiments, test compounds and libraries containing test compounds can be obtained by systematically altering the structure of a first test compound, e.g., a first test compound with known properties, e.g., the property of binding to or interacting with FcRn and/or albumin, or a compound that is structurally similar to such a compound. In some embodiments, the structure of a first test compound and/or a systematically altered test compound exhibits a structure that is correlated to a resulting biological activity (a structure-activity relationship), and one of ordinary skill in the art can use such a structure-activity relationship as a starting point for the systematic alteration of test compounds. In some instances, the systematic alteration may be largely empirical, while in other instances, the three-dimensional structure of test compound can be used as a starting point for the rational design of a small molecule compound or compounds.

In some embodiments, a compound to be screened according to one or more methods described herein is a nucleic acid. Nucleic acids to be screened according to one or more methods disclosed herein can be naturally occurring, e.g., DNA or RNA. Nucleic acids to be screened according to one or more methods disclosed herein can also be non-naturally occurring. For example, nucleic acids with modified backbones such as, without limitation, peptide nucleic acids (PNAs), morpholino and locked nucleic acids (LNAs), glycol nucleic acids (GNAs) and threose nucleic acids (TNAs) can be screened. Other modifications of nucleic acid molecules are within the skill of those of ordinary skill in the art, and such modified nucleic acids can be screened according to one or more methods disclosed herein.

In some embodiments, naturally occurring nucleic acid sequences can be screened. Alternatively, non-naturally occurring nucleic acid sequences can be screened. In some embodiments, a naturally occurring nucleic acid can be fused with a non-naturally occurring nucleic acid, which fusion nucleic acid can be screened by one or more methods described herein. As an additional example, one or more nucleic acid residues of a naturally occurring nucleic acid can be altered, such that the engineered nucleic acid differs from the naturally occurring nucleic acid at one or more positions. In some embodiments, one or more nucleic acid residues of a naturally occurring nucleic acid are altered to generate an engineered nucleic acid such that the engineered nucleic acid is at least 50%, e.g., 50%, 55%, 60%, 65%, 70%, 75%, 80%, 85%, 90%, 95%, 96%, 97%, 98%, 99% or higher, identical to the naturally occurring nucleic acid. As will be understood by those of ordinary skill in the art, nucleic acids can be chemically modified (e.g., glycosylated, pegylated, etc.). Such modified nucleic acids can also be screened by one or more methods described herein.

Nucleic acids to be screened can be either single- or double-stranded. Such double-stranded nucleic acids need not be perfectly double-stranded. For example, one or more nucleic acid residues of an otherwise double-stranded nucleic acid may be unpaired (e.g., bulged out). In some embodiments, nucleic acids to be screened are partially double-stranded, such that a portion of the nucleic acid is single-stranded and a portion is double-stranded. In some embodiments, three or more nucleic acid strands interact (e.g., via basepairing) to form a multi-stranded nucleic acid, and such a multi-stranded nucleic acid may be screened according to one or more methods disclosed herein. Nucleic acids to be screened according to one or more methods described herein can be of any length. In some embodiments, nucleic acids to be screened will be less that about 1000 residues in length, e.g., less than about 1000, less than about 900, less than about 800, less than about 700, less than about 600, less than about 500, less than about 400, less than about 300, less than about 200, less than about 100, less than about 90, less than about 80, less than about 70, less than about 60, less than about 50, less than about 40, less than about 30, less than about 20, less than about 10, less than about 5, or fewer residues in length. In some embodiments, nucleic acids to be screened will be at least 5 residues in length, e.g., at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000 or more residues in length.

In some embodiments, a compound to be screened according to one or more methods described herein is an antibody or an antibody fragment. The term "antibody" as used herein refers to an immunoglobulin molecule that contains one or more antigen binding sites which specifically bind (immunoreact with) an antigen. The term "antibody fragment" as used herein refers to an immunologically active portion of an immunoglobulin molecule, such as a Fab or F(ab')2 fragment, that contains one or more antigen binding sites which specifically bind (immunoreact with) an antigen.

In some embodiments, an antibody to be used in the present methods (e.g., is a monoclonal antibody. As is understood in the art, a monoclonal antibody is derived from a clonal population of antibody molecules that contain only one species of an antigen binding site, such that the monoclonal antibody binds one particular epitope of an antigen. In some embodiments, a monoclonal antibody is engineered to be a chimeric or humanized antibody. Chimeric antibody molecules can include, for example, an antigen binding domain from an antibody of a mouse, rat, or other species, with human constant regions. A variety of approaches for making chimeric antibodies have been described. See e.g., Morrison et al., Proc. Natl. Acad. Sci. U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B, each of which is hereby incorporated by reference in its entirety. A humanized antibody is a chimeric antibody wherein the large majority of the amino acid residues are derived from human antibodies, thus minimizing any potential immune reaction when delivered to a human subject. In humanized antibodies, amino acid residues in the complementarity determining regions are replaced, at least in part, with residues from a non-human species that confer a desired antigen specificity or affinity. Such altered immunoglobulin molecules can be made by any of several techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and are preferably made according to the teachings of PCT Publication WO92/06193 or EP 0239400, each of which is hereby incorporated herein by reference in its entirety). Humanized antibodies can be commercially produced by, for example, Scotgen Limited, 2 Holly Road, Twickenham, Middlesex, Great Britain. For further reference, see Jones et al., Nature 321:522-525 (1986); Riechmann et al., Nature 332:323-329 (1988); and Presta, Curr. Op. Struct. Biol. 2:593-596 (1992), each of which is hereby incorporated herein by reference in its entirety.

In some embodiments, an antibody to be used in a method described herein is a polyclonal antibody. As is understood in the art, a polyclonal antibody is composed of a population of antibody molecules that contain multiple species of antigen binding sites. Polyclonal antibodies typically interact with a particular antigen, e.g., one or more epitopes of that antigen. Polyclonal antibodies are typically produced by immunizing a host with an antigen. In some cases, such an antigen contains more than one epitope. In some embodiments, a polyclonal antibody to be screened using one or more methods disclosed herein binds to an FcRn polypeptide. In some embodiments, a polyclonal antibody to be screened using one or more methods disclosed herein binds to an albumin polypeptide.

In some embodiments, the test compound is a variant albumin polypeptide, as described herein.

The test compounds described above are exemplary in nature and are not meant to be limiting. Those of ordinary skill in the art will be aware of other suitable test compounds, and will be able to screen them for the ability to disrupt the interaction between FcRn and albumin using one or more methods disclosed herein.

Identification of Albumin Variants that are Deficient in Binding FcRn

In some embodiments, methods of identifying a variant albumin polypeptide that is deficient in binding an FcRn polypeptide are disclosed. In some embodiments, such methods comprise contacting the FcRn polypeptide with the variant albumin polypeptide and determining the binding of the variant albumin polypeptide to the FcRn polypeptide, wherein a decrease in binding between the FcRn polypeptide and the variant albumin polypeptide compared to binding that would occur between the FcRn polypeptide and a reference albumin polypeptide indicates that the variant albumin polypeptide is deficient in binding the FcRn polypeptide. In some embodiments, the reference albumin polypeptide is a wild type albumin polypeptide. In some embodiments, the reference albumin polypeptide is a human albumin polypeptide. In some embodiments, the reference FcRn polypeptide is a wild type FcRn polypeptide. In some embodiments, the reference FcRn polypeptide is a human FcRn polypeptide. In some embodiments, the FcRn polypeptide is expressed on the surface of a cell.

Any of a variety of methods to detect a variant albumin polypeptide that is deficient in binding FcRn may be used. For example, fluorescence resonance energy transfer ("FRET") methods may be used. FRET occurs when an excited donor fluorophore transfers its energy to an acceptor fluorophore in close proximity. Thus, if a first molecule (e.g., FcRn) and a second molecule (e.g. albumin) are suspected of binding, the first molecule can be tagged with a first fluorescent label that upon excitation emits radiation of a given wavelength. If the second molecule is labeled with a second fluorescent label, which second fluorescent label is excited by the emission radiation of the first label, binding of the first and second molecules can be detected or measured by exciting the first molecule containing the first label, and detecting or measuring emission radiation of the second molecule containing the second label. In some embodiments, the first and second labels are excited by different wavelengths. In such embodiments, excitation of the first label will be expected to have little or no direct effect on excitation of the second label. In some embodiments, the excitation wavelengths of the first and second labels overlap. In such embodiments, excitation of the first label will also directly excite the second label to at least some extent. Thus, in detecting or measuring binding, the emission of the second label will need to be corrected for the additional excitation.

In some embodiments, a variant albumin polypeptide is labeled with a donor fluorophore and FcRn is labeled with an acceptor fluorophore. If the variant albumin polypeptide is deficient in binding FcRn, a decrease in the emission radiation of from the acceptor fluorophore on FcRn will result. Similarly, a variant albumin polypeptide may be labeled with an acceptor fluorophore and FcRn may be labeled with an acceptor fluorophore. If the variant albumin polypeptide is deficient in binding FcRn, a decrease in the emission radiation of from the acceptor fluorophore on the variant albumin polypeptide will result.

In some embodiments, detection and identification of a variant albumin polypeptide that is deficient in binding FcRn may be achieved by chromatographic methods. For example, after incubating FcRn with a variant albumin polypeptide, the FcRn or the variant albumin polypeptide may be isolated. Isolation may be performed by any of a variety of techniques including, without limitation, column chromatography, antibody pull-downs, fractionation, etc. If FcRn and the variant albumin polypeptide bind, isolation of one polypeptide will result in isolation of the other. Standard chromatographic methods known to those skilled in the art may be used. In some embodiments, the FcRn, the variant albumin polypeptide or both can be labeled (e.g. with a radioactive or non-radioactive label) to facilitate detection of the polypeptide after isolation. In some embodiments, neither polypeptide is labeled, and the polypeptides are detected by standard techniques such as, without limitation, Western blotting, mass spectrometry, or antibody staining.

Those of ordinary skill in the art will be aware of these and other techniques that may be used to detect and identify a variant albumin polypeptide that is deficient in binding FcRn. In some embodiments, the amount by which a variant albumin polypeptide is deficient in binding FcRn can be expressed as percentage of the binding that would occur with a wild type albumin. For example, a variant albumin polypeptide can bind FcRn about 10% as well as a wild type albumin polypeptide binds FcRn, e.g., about 10%, about 15%, about 20%, about 25%, about 30%, about 35%, about 40%, about 45%, about 50%, about 55%, about 60%, about 65%, about 70%, about 75%, or more as well as a wild type albumin polypeptide binds FcRn. In some embodiments, a variant albumin polypeptide can bind FcRn about 50% as well as a wild type albumin polypeptide binds FcRn, e.g., about 50%, about 55%, about 60%, about 65%, about 70%, about 75%, about 80%, about 85%, about 90%, or more as well as a wild type albumin polypeptide binds FcRn. In some embodiments, a variant albumin polypeptide can bind FcRn about 90% as well as a wild type albumin polypeptide binds FcRn, e.g., about 90%, about 91%, about 92%, about 93%, about 94%, about 95%, about 96%, about 97%, about 98%, about 99% or more as well as a wild type albumin polypeptide binds FcRn. In general, the less well a variant albumin polypeptide binds FcRn, the greater its utility as a therapeutic. In some cases, however, it will be desirable to identify a variant albumin polypeptide that binds FcRn to a certain minimal percent as compared to wild type albumin binding. Those of ordinary skill in the art will be aware of such cases, and will be able to use methods described herein to identify such a compound.

Variant Albumin Polypeptides

In some embodiments, methods disclosed herein may be used to screen for a variant albumin polypeptide that is deficient in FcRn binding. In some embodiments, such a variant albumin polypeptide is engineered polypeptide that includes one or more amino acid residues that differ from a wild type albumin polypeptide. In some embodiments, such a variant albumin polypeptide includes one or more amino acid additions, deletions or substitutions as compared to a wild type albumin polypeptide. A variant albumin polypeptide can be an engineered albumin polypeptide that is similar in sequence identity to a wild type albumin. For example, a variant albumin polypeptide can be at least 50%, e.g., at least 50%, at least 55%, at least 60%, at least 65%, at least 70%, at least 75%, at least 80%, at least 85%, at least 90%, at least 95%, at least 96%, at least 97%, at least 98%, at least 99% or more identical to a wild type albumin polypeptide.

In some embodiments, the variant albumin polypeptide includes one or more portions of a wild type albumin, e.g., is truncated on either or both of the C terminus or the N terminus, or has a deletion in the middle. The truncations or deletions can be up to, e.g., 10%, 20%, 30%. 40%, 50%, 55%, 60%, 65%, 70%, 75%, 80%, 85%, or 90% of the full length wild type albumin.

In some embodiments, a variant albumin polypeptide to be screened according to one or more methods disclosed herein can include at least a portion of a wild type albumin amino acid sequence, but be engineered to differ from wild type albumin. For example, a wild type albumin polypeptide can be fused to an exogenous polypeptide sequence, either naturally or non-naturally occurring, to generate a fusion polypeptide, which fusion polypeptide is a variant albumin polypeptide. Additionally or alternatively, a fragment of a wild type albumin polypeptide can be screened using one or more methods described herein. Such a fragment is considered a variant albumin polypeptide. In some embodiments, a fragment of an albumin polypeptide can be fused to an exogenous polypeptide sequence, either naturally or non-naturally occurring, to generate a fusion polypeptide. Such a fusion polypeptide containing an albumin fragment is also a variant albumin polypeptide.

In some embodiments, a variant albumin polypeptide is a chimeric albumin polypeptide comprising portions from two or more wild type albumin polypeptides. In some embodiments, such a chimeric albumin polypeptide may be further modified such that it contains non-wild type amino acid residues at given positions. Such chimeric albumin polypeptides can be further modified in any of the variety of ways described herein.

As will be understood by those of ordinary skill in the art, polypeptides can be chemically modified (e.g., glycosylated, or pegylated). In some embodiments, an albumin polypeptide or fragment thereof is chemically modified to generate another type of variant albumin polypeptide, which variant albumin polypeptide can be screened according to one or more methods disclosed herein. Any of a variety of chemical modifications are within the skill of those skilled in the art, and can be screened according to one or more of the presently disclosed methods.

In some embodiments the variant albumin protein, or fragment thereof, differs from the wild type sequence by at least one but by less than 15, 10 or 5 amino acid residues. In some embodiments the variant differs from the corresponding sequence by at least one residue, but less than 20%, 15%, 10% or 5% of the residues in it differ from the corresponding sequence. (If this comparison requires alignment the sequences should be aligned for maximum homology. "Looped" out sequences from deletions or insertions, or mismatches, are considered differences.) The differences can be changes at essential or non-essential residues, and conservative or non-conservative substitutions.

In some embodiments, the albumin variant includes an amino acid sequence that is at least about 50%, 55%, 60%, 65%, 70%, 75%, 80%, 85%, 90%, 95%, 98% or more homologous to the corresponding wild type sequence.

In general, the variant albumin polypeptides will not bind to FcRn, but will bind to one or more of Protein G, bilirubin, bile acid, fatty acid, thyroxin, propofol, 2: oxyphenbutazone, diflunisal, diazepam, halothane, ibuprofen, indoxyl sulfate, 2: CMPF, azapropazone, indomethacin, phenylbutazone, warfarin, 2': indoxyl sulfate, 3': diflunisal, 2': iodipamide, and hemin (see, e.g., Varshney et al., *Ligand binding strategies of human serum albumin: how can the cargo be utilized*, Chirality; 2009, incorporated herein by reference in its entirety). In some embodiments, the methods described herein include a step of determining whether the variant albumin polypeptides still bind to one or more of Protein G, bilirubin, bile acid, fatty acid, thyroxin, propofol, 2: oxyphenbutazone, diflunisal, diazepam, halothane, ibuprofen, indoxyl sulfate, 2: CMPF, azapropazone, indomethacin, phenylbutazone, warfarin, 2': indoxyl sulfate, 3': diflunisal, 2': iodipamide, and hemin.

The variant albumin polypeptides described above are exemplary in nature and are not meant to be limiting. Those of ordinary skill in the art will be aware of other suitable variant albumin polypeptides as well as methods of making such variant albumin polypeptides, and will be able to screen them using one or more of the presently disclosed methods to determine which are deficient in their ability to bind FcRn.

Screening in Vitro

Both recombinant and non-recombinant polypeptides can be used in various screening methods disclosed herein. In some embodiments, a recombinant FcRn polypeptide, a recombinant albumin polypeptide, or both may be expressed in a host cell or in vitro and used in one or more screening methods described herein. Routine molecular biological techniques may be used to express such polypeptides in a host cell or in vitro. Such techniques are described, for example, in Sambrook, Fritsch & Maniatis, Molecular Cloning: A Laboratory Manual, 2nd Ed., Cold Spring Harbor Press N.Y., 1989. Those of ordinary skill in the art will be aware of these and additional techniques that may be used to express a recombinant FcRn polypeptide, a recombinant albumin polypeptide, or both in a host cell or in vitro.

As a non-limiting example, a recombinant FcRn polypeptide, a recombinant albumin polypeptide, or both may be expressed according to the following general protocol. A nucleic acid sequence encoding an FcRn polypeptide, an albumin polypeptide, or both may be isolated from a cell or nucleic acid preparation by any of a variety of techniques including, without limitation, restriction endonuclease digestion, PCR, and chromatography. The isolated nucleic acid sequence may be amplified (e.g., by PCR) or, if a sufficient amount of nucleic acid has been obtained, the isolated nucleic acid sequence may be used directly. After isolation, the nucleic acid sequence may be inserted into an expression vector. As is known to those of ordinary skill in the art, expression vectors contain regulatory sequences that are able to direct expression of a polypeptide from a nucleic acid sequence encoding that polypeptide under appropriate conditions. A wide variety of expression vectors are known, and those of ordinary skill in the art will be able to choose a suitable vector according to their experimental needs. After insertion into the expression vector, the vector containing the isolated nucleic acid sequence may be transformed into a host cell for amplification. In some embodiments, the inserted nucleic acid sequence may optionally be ligated prior to transformation.

After amplification, the vector containing the inserted nucleic acid sequence may be isolated from the host cell, and subjected to conditions that result in production of expression of the polypeptide encoded by the isolated nucleic acid sequence (e.g., an FcRn polypeptide or an albumin polypeptide). Alternatively, the host cell may be subjected to conditions that result in production of expression of the polypeptide encoded by the isolated nucleic acid sequence. For example, certain expression vectors contain inducible promoters that become active upon exposure to one or more factors. After the polypeptide has been expressed in vitro or in the host cell, the polypeptide may be purified by any of a variety of routine techniques known to those of ordinary skill in the art.

In some embodiments, a non-recombinant FcRn polypeptide, a non-recombinant albumin polypeptide, or both may be isolated from a cell or an animal. For example, non-recombinant albumin may be isolated from the blood of an animal using routine techniques such as fractionation, chromatography, etc. In some embodiments, a combination of recombinant and non-recombinant polypeptides can be used in various screening methods disclosed herein. For example, a recombinant FcRn polypeptide can be contacted with a non-recombinant albumin polypeptide (e.g., a naturally occurring albumin polypeptide isolated from blood) in the presence of a test compound to determine that compound's effect on binding between FcRn and albumin.

Cells

Any type of cell or bacteria that can express an FcRn polypeptide can be used in one or more methods to identify compounds that disrupt the binding between FcRn and albumin, or to identify variant albumin polypeptides that are deficient in FcRn binding, as described herein. See e.g., Anderson J T et al. J Im Methods. 2008. Feb. 29; 331(1-2):39-49, incorporated herein by reference in its entirety. In general, suitable cell types include cells of such as Chinese hamster ovary (CHO) cells available from the ATCC as CCL61, NIH Swiss mouse embryo cells NIH/3T3 (ATCC CRL 1658), HELA cells (ATCC CCL 2), baby hamster kidney cells (BHK), COS-7, COS-1, HEK293 (ATCC CRL 1573), Ltk-1, AV-12 (ATCC CRL 9595), and the like. Those of ordinary skill in the art will be aware of suitable cell lines, as well as methods of handling such cell lines such that they can be used in accordance with one or more methods disclosed herein. Albumin or albumin fragments can be made from yeast, such as *pichia pastoris*.

In some embodiments, a cell that does not normally express FcRn can be used in accordance with various methods described herein. In such embodiments, a cell is transformed (e.g., stably or transiently) with a nucleic acid molecule that can direct expression of an FcRn polypeptide under suitable conditions. For example, a vector containing an FcRn coding region operably linked to a promoter that is able to function in a given cell can be transformed into that cell such that, under suitable conditions, the promoter directs expression of the FcRn coding region to generate an FcRn polypeptide. In some embodiments, a promoter is constitutive such that it constitutively directs FcRn expression. In some embodiments, a promoter is inducible such that it only directs FcRn expression under certain conditions (e.g., below a given temperature) or in response to certain factors. Controlling such conditions or factors permits the practitioner to control whether and when the FcRn polypeptide is expressed in the cell.

Animal Models

In some embodiments, screening for a compound that disrupts the interaction between FcRn and albumin or for a variant albumin polypeptide that is deficient in binding FcRn can occur in an animal model. For example, a test compound can be administered to an animal that expresses both FcRn and albumin, and the binding between the expressed FcRn and albumin can be determined A decrease in binding between FcRn and albumin in the presence of the administered compound indicates that the compound disrupts the binding. Alternatively, a variant albumin polypeptide can be administered to the animal and its binding to FcRn determined. A decrease in binding between the variant albumin polypeptide compared to the binding of wild type albumin to FcRn indicates that the variant albumin polypeptide is deficient in FcRn binding.

In some embodiments, methods of identifying compounds that disrupt an interaction (e.g., binding) between an FcRn polypeptide and an albumin polypeptide include administering the test compound to a subject, e.g., an experimental animal (e.g., a mammal) expressing the FcRn polypeptide and the albumin polypeptide with a test compound and determining the level of the albumin polypeptide in a body fluid of the subject, wherein a difference in the level of albumin polypeptide in the body fluid of the subject in the presence of the compound compared to the level of albumin polypeptide that would be present in the body fluid of the animal in the absence of the test compound indicates that the test compound disrupts the interaction between the FcRn polypeptide and the albumin polypeptide. In some embodiments, prior to administration to the subject, the test compound is first tested in vitro to determine its effect on an interaction (e.g., binding) between an FcRn polypeptide and an albumin polypeptide. In some embodiments, prior to administration to the subject, the test compound has not been tested in vitro to determine its effect on an interaction (e.g., binding) between an FcRn polypeptide and an albumin polypeptide. In some embodiments, a test compound can be a polypeptide, a small molecule, a nucleic acid, an antibody, and/or an antibody fragment. In some embodiments, the body fluid is bile, urine, or feces, and an increase in the level of albumin polypeptide present in the bile, urine, or feces indicates that the compound disrupts the interaction between the FcRn polypeptide and the albumin polypeptide. In some embodiments, the body fluid is blood or lymph, and a decrease in the level of albumin polypeptide present in the blood or lymph indicates that the compound disrupts the interaction between the FcRn polypeptide and the albumin polypeptide. In some embodiments, the subject expresses a wild type albumin polypeptide. In some embodiments, the subject expresses a human albumin polypeptide. In some embodiments, the subject expresses a wild type FcRn polypeptide. In some embodiments, the subject expresses a human FcRn polypeptide. In some embodiments, the subject is contacted with the compound by intravenous administration, intradermal administration, subcutaneous administration, oral administration, transdermal administration, transmucosal administration, and/or rectal administration.

In some embodiments, binding between FcRn and albumin or a variant albumin polypeptide is determined in an animal model by determining the level of albumin or variant albumin polypeptide present in a body fluid where albumin levels are normally relatively high such as blood, lymph or both. A decrease in the level of albumin or variant albumin polypeptide present in blood, lymph or both indicates that the compound disrupts binding between FcRn and albumin, or that the variant albumin polypeptide is deficient in binding FcRn. In some embodiments, binding between FcRn and albumin or a variant albumin polypeptide is determined in an animal model by determining the level of albumin or variant albumin polypeptide present in a body fluid where albumin levels are normally relatively low such as bile, urine, or feces. An increase in the level of albumin or variant albumin polypeptide present in bile, urine, or feces indicates that the compound disrupts binding between FcRn and albumin, or that the variant albumin polypeptide is deficient in binding FcRn.

In some embodiments, an animal model for screening compounds that disrupt the interaction between FcRn and albumin can be a non-human animal that expresses both FcRn and albumin. In some embodiments, an animal model for screening variant albumin polypeptides that are deficient in binding FcRn can be a non-human animal that expresses at least FcRn. Such non-human animals include, without limitation, mammals, e.g., mice, rats, non-human primates, sheep, dog, and cow.

In some embodiments, an animal to be used in accordance with one or more methods disclosed herein can be a transgenic animal. For example, an animal to be used in accordance with one or more methods disclosed herein can be transgenic such that it expresses FcRn, albumin, or both. In some embodiments, an animal can be transgenic such that it expresses a human FcRn, albumin, or both. For example, the endogenous FcRn gene(s), albumin gene(s), or both can be disrupted in the animal and human versions of these genes can be introduced into the animal. Such animals are useful in screening for compounds that disrupt the interaction between human FcRn and human albumin, or for screening for variant albumin polypeptides that are deficient in binding human FcRn.

Transgenic non-human animals are typically produced by introducing a transgene into the germline of the non-human animal. Embryonic stem (ES) cells are the primary type of target cell for introduction of the transgene into the non-human animal in order to achieve homologous recombination. ES cells are obtained from pre-implantation embryos cultured in vitro and fused with embryos (see e.g., Evans et al. (1981) Nature 292, 154 156; Bradley, M. O., et al. (1984) Nature 309, 255 258; Gossler, et al. (1986) Proc. Natl. Acad. Sci U.S.A. 83, 9065 9069; and Robertson, et al. (1986) Nature 322, 445 448, each of which is incorporated herein by reference in its entirety). Transgenes can be efficiently introduced into the ES cells by DNA transfection or by retrovirus-mediated transduction. Such transformed ES cells can thereafter be combined with blastocysts from a non-human animal The ES cells thereafter colonize the embryo and contribute to the germ line of the resulting chimeric animal. For review see Jaenisch, R. (1988) Science 240, 1468 1474, incorporated herein by reference in its entirety. The transfected embryonic cells may be incubated in vitro for varying amounts of time, or reimplanted into the surrogate host, or both. Those of ordinary skill in the art will be aware of these and other suitable methods for generating transgenic non-human animals.

Methods of Treatment, Pharmaceutical Compositions and Methods of Administration

The methods described herein include methods for the treatment of disorders associated with albumin-binding toxins (e.g., with toxic levels of such toxins), e.g., from an overdose (e.g., from accidental or intentional exposure or ingestion to an amount of a toxin above a level considered safe for human or animal health) or from an endogenously high level of an albumin-binding toxin in a subject (e.g., from the subject producing a higher level of the toxin than what is considered normal and safe for human or animal health). In some embodiments, the disorder is due to an overdose or a high level of copper, hematin, long-chain fatty acid, zinc, bilirubin, thyroxine, eicosanoids, tryptophan, vitamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, quinidine, ricin, and acetaminophen. Generally, the methods include administering a therapeutically effective amount of therapeutic compound as described herein, to a subject who is in need of, or who has been determined to be in need of, such treatment.

The terms "effective amount" and "effective to treat," as used herein, refer to an amount or a concentration of a compound utilized for a period of time (including acute or chronic administration and periodic or continuous administration) that is effective within the context of its administration for causing an intended effect or physiological outcome. As used in this context, to "treat" means to ameliorate at least one symptom of the disorder associated with an albumin-binding toxin, e.g. a symptom resulting from an overdose or a toxic level of an albumin-binding toxin. An overdose or a toxic level of an albumin-binding toxin can results in many detrimental effects, e.g., death, organ damage, or neurological damage; thus, a treatment can result in a reduction in these effects. Administration of a therapeutically effective amount of a compound described herein for the treatment of a condition associated with an albumin-binding toxin will result in decreased, e.g., rate of mortality.

Compounds useful in decreasing the concentration of albumin-binding toxins or treating disorders associated with albumin-binding toxins, e.g., compounds identified in screens described herein, can be incorporated into pharmaceutical compositions. Such compositions typically include the compound and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Sterile injectable solutions can be prepared by incorporating the active compound in the required amount in an appropriate solvent with one or a combination of ingredients enumerated above, as required, followed by filtered sterilization.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

The compounds can also be prepared in the form of suppositories (e.g., with conventional suppository bases such as cocoa butter and other glycerides) or retention enemas for rectal delivery.

In some embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the patient to be treated; each unit containing a predetermined quantity of active compound calculated to produce the desired therapeutic effect in association with the required pharmaceutical carrier.

The pharmaceutical compositions can be included in a container, pack, or dispenser together with instructions for administration.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

Data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The skilled artisan will appreciate that certain factors influence the dosage and timing required to effectively treat a patient, including but not limited to the type of patient to be treated, the severity of the disease or disorder, previous treatments, the general health and/or age of the patient, and other disorders present. Moreover, treatment of a patient with a therapeutically effective amount of a protein, polypeptide, antibody, or other compound can include a single treatment, or can include a series of treatments.

Certain embodiments of methods and compositions provided herein are further illustrated by the following examples. The examples are provided for illustrative purposes only. They are not to be construed as limiting the scope or content of the invention in any way.

EXAMPLES

Example 1

Serum and Bile Measurements

Figure 2:
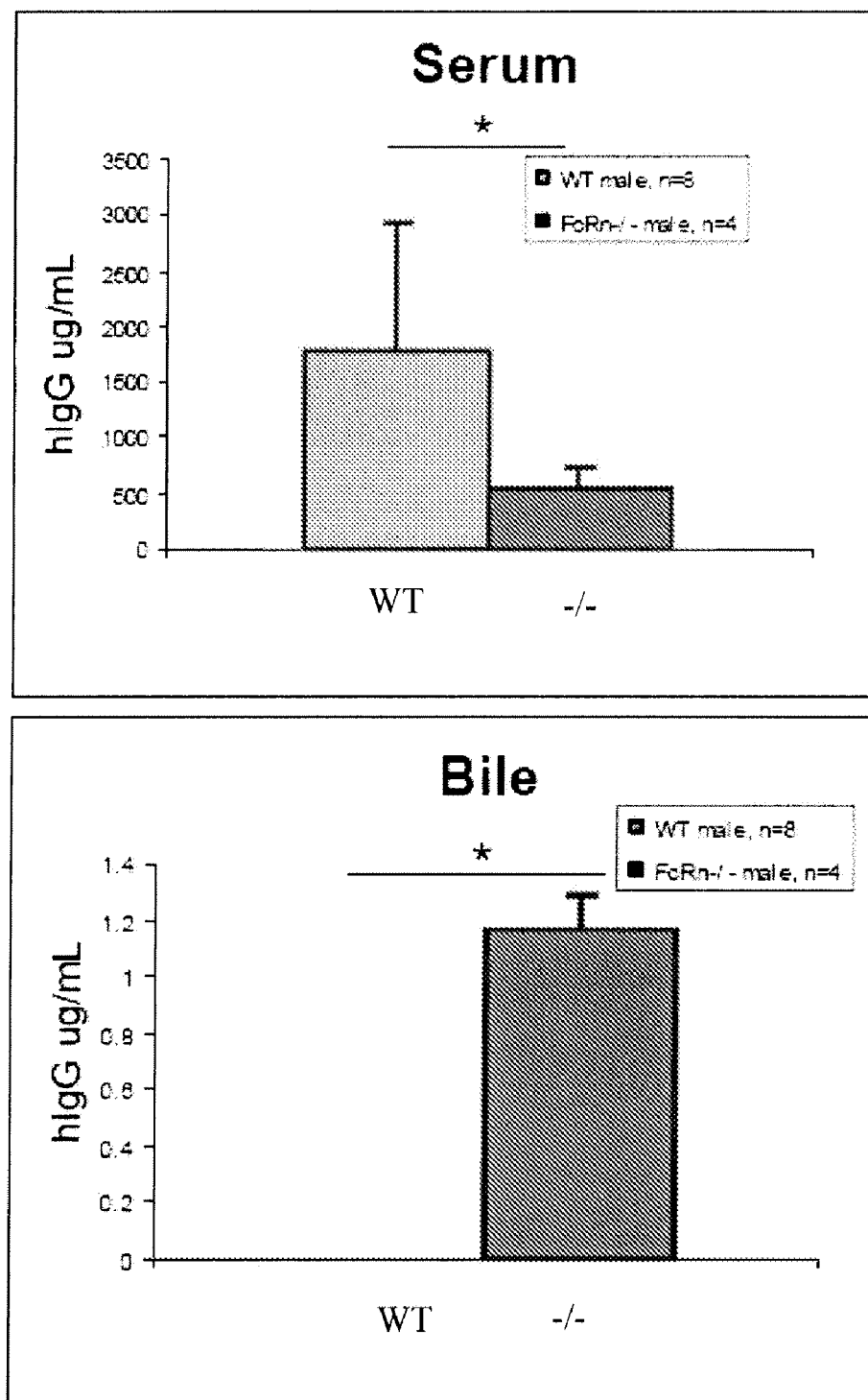
FIG. 2 is a pair of bar graphs showing that elevated levels of human IgG were detected in the bile of FcRn deficient (−/−) mice 24 hours after infusion of human IgG via tail vein.
Figure 3:
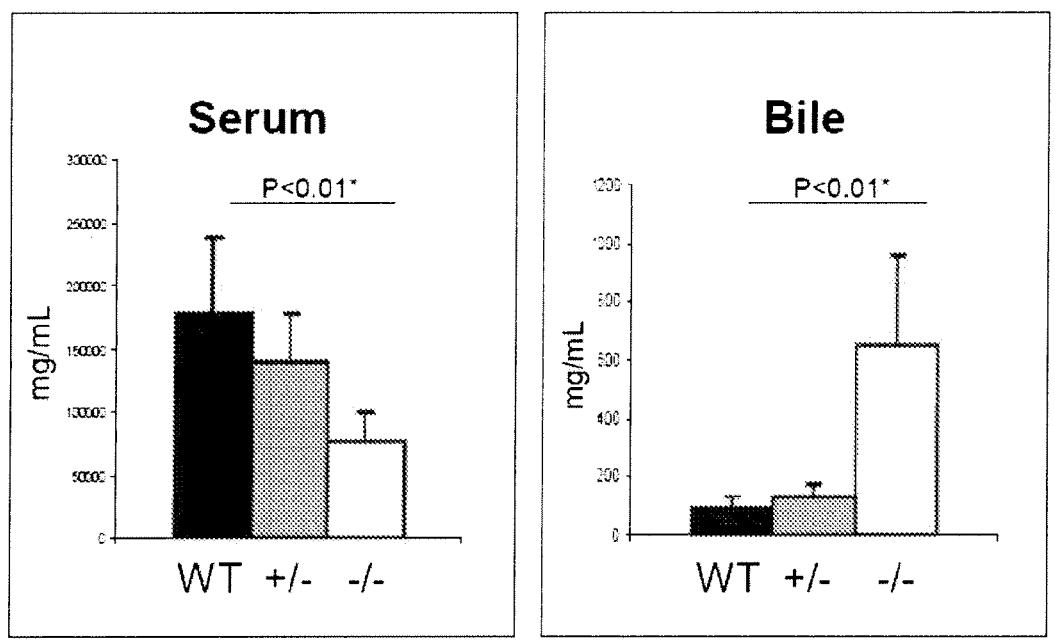
FIG. 3 is a pair of bar graphs showing elevated levels of mouse albumin in the bile of FcRn deficient mice.

Human IgG and rat albumin were administered via the tail vein to wild-type (WT) or FcRn deficient (−/−) mice 24 hours prior to the harvest of serum and bile. For serum and bile measurements, mice were euthanized before blood was removed via the heart and the bile was removed via the gallbladder. Concentration of IgG and albumin were measured by ELISA. Results are shown in FIGS. 1, 2, and 3). Similar results were obtained from bile collected via common bile duct cannulation.

Example 2

Infusion Studies

Figure 4:
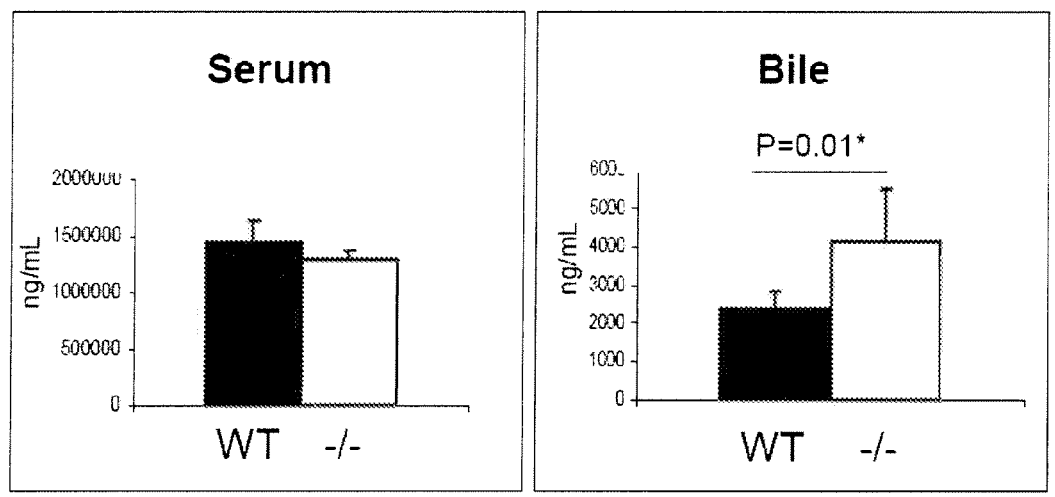
FIG. 4 is a pair of bar graphs showing that elevated levels of rat albumin were detected in the bile of FcRn deficient mice 24 hours after infusion of rat albumin.

For the human IgG, human albumin, and rat albumin infusions studies, mice were injected with 200 uL volume via the tail vein. After 24 hours, blood/serum and gallbladder bile were removed as described in Example 1. Results are shown in FIG. 4.

Examples 1 and 2 show that FcRn in the liver mediates transport of IgG and albumin from bile to circulation thus functioning as a scavenger receptor for these two important proteins to rescue them from leakage into the bile.

Example 3

Bidirectional Transcytosis Assay

Figure 5:
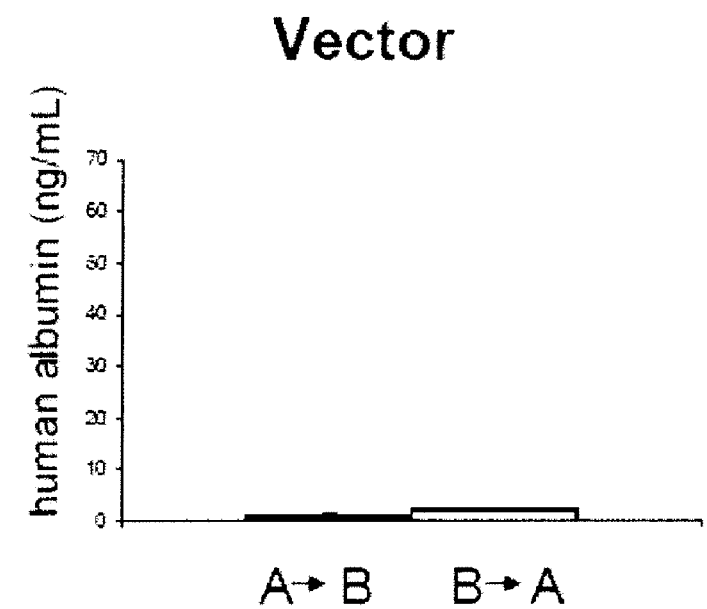
FIG. 5 is a pair of bar graphs showing that human FcRn mediates bidirectional transport of human albumin across MDCK II cells that expresses human FcRn and human beta-2-microglobulin.
Figure 5:
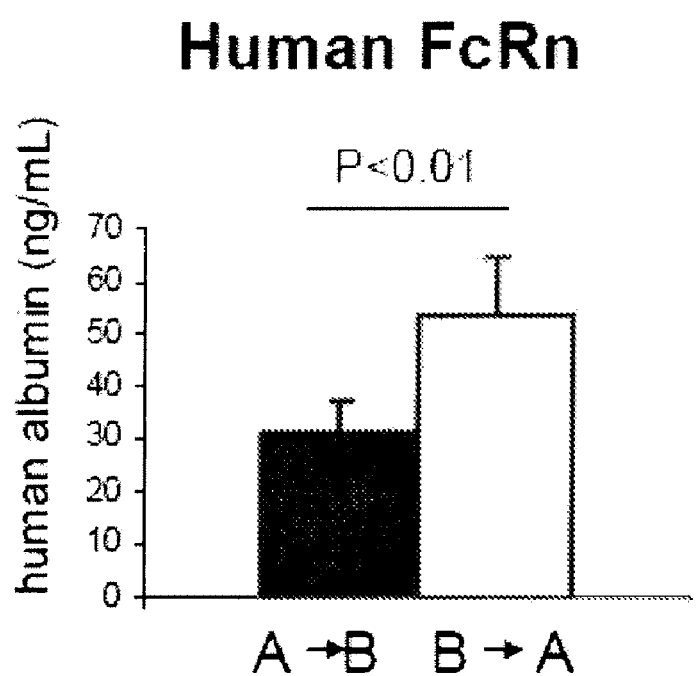

MDCK II cells with or without expression of human (h) FcRn and hβ2 were grown on transwell membranes before input of human albumin to the apical or basolateral chamber. Cells were grown to confluence on 12 mm, 0.4 mm polycarbonate membrane transwells (Corning) and the transepithelial resistance was determined by resistance meter as described above. The transwells were washed in Hank's Balanced Salt solution (HBSS) (Sigma) pH 6 and subsequently in pH 7.4. This was followed by a 20-minute equilibration with HBSS pH 6 at the side anticipated to receive albumin and HBSS pH 7.4 at the contralateral side of the monolayer. Albumin equilibrated in HBSS pH 6 was added to the input chamber of the transwell and allowed to incubate for 120 minutes at 37° C. with 5% CO2 environment. The output chamber fluid was then removed, and the albumin concentrations measured by ELISA. Results are shown in FIG. 5.

This example shows that FcRn can also mediate the bidirectional transport of albumin across epithelial cells, as was previously demonstrated for IgG.

Example 4

Mortality Assay (1)

Figure 6:
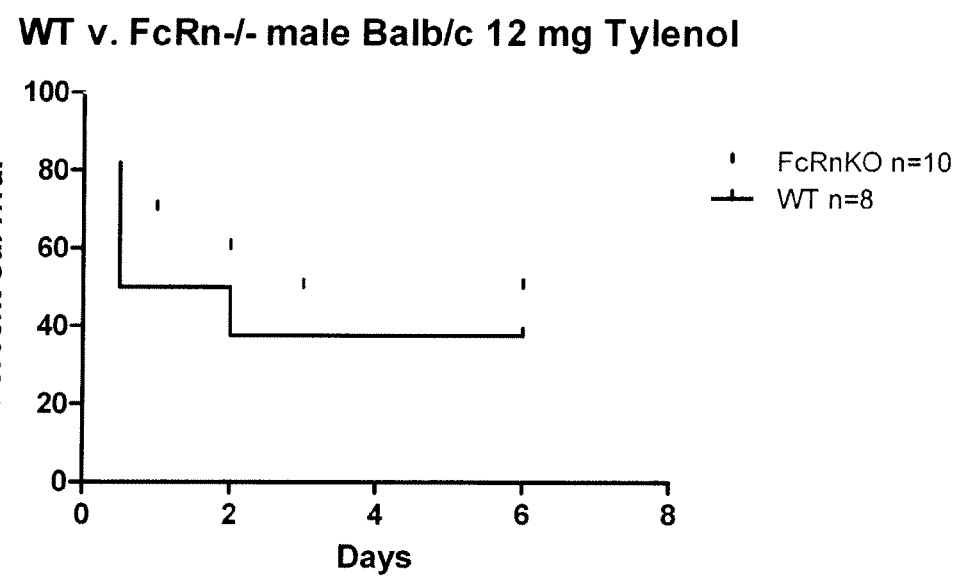
FIG. 6 is a line graph showing that mice deficient in FcRn (gray line) has decreased mortality compared to wild-type mice (black line) when given 12 mg of acetaminophen.

Wild-type Balb/c mice and Balb/c mice deficient in FcRn were administered 12 mg of acetaminophen. The dose administered is equivalent to 42 g in a 70 kg human (84 tabs of 500 mg extra strength Tylenol™ (acetaminophen)). FIG. 6 shows that mice deficient in FcRn (which has lower serum albumin and IgG levels) had decreased mortality compared to wild-type mice when given 12 mg of acetaminophen.

This example demonstrates that decreasing the available amount of albumin by disrupting the interaction between albumin and FcRn could decrease the toxicity of compounds that bind to albumin. Since albumin is known to bind to acetaminophen, the half-life of acetaminophen was likely increased in wild-type mice, and thus prolonging the toxicity. The increased survival rate of mice deficient in FcRn was likely due to a decrease in the amount of albumin-bound acetaminophen, and thus enhancing degradation of acetaminophen. Furthermore, in view of the data described herein, the albumin-bound acetaminophen in the FcRn−/− mice was also likely lost through the biliary tract in the absence of FcRn, and thus increasing the removal of acetaminophen.

Example 5

Mortality Assay (2)

Mice deficient in mouse FcRn that express human FcRn (hFcRn) and hβ2m are administered a lethal dose of acetaminophen (e.g., about 12 mg of acetaminophen) with (Group I) or without (Group II) a compound that blocks the interaction between FcRn and albumin. The compound is a mouse anti-hFcRn antibody that blocks the hFcRn-albumin binding site (but not hFcRn-IgG binding site) (the ADM31 antibody, described in Qiao et al., Proc Natl Acad Sci USA. 105(27): 9337-42 (2008)). Mortality of the two groups of mice are determined. The example tests whether administration of a compound that blocks the interaction between FcRn and albumin can treat disorders or effects associated with albumin-binding toxins.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a candidate compound for decreasing the concentration of an albumin-binding toxin in a subject, the method comprising:
contacting (a) a test compound, (b) an FcRn polypeptide or albumin-binding fragment thereof, and (c) an albumin polypeptide or FcRn-binding fragment thereof, under conditions and for a time sufficient to allow binding between the FcRn polypeptide or fragment thereof and the albumin polypeptide or fragment thereof and
detecting whether the test compound inhibits binding between the FcRn polypeptide or fragment thereof and the albumin polypeptide or fragment thereof
wherein a test compound that inhibits binding between the FcRn polypeptide or fragment thereof and the albumin polypeptide or fragment thereof is a candidate compound for decreasing the concentration of an albumin-binding toxin in a subject.

2. The method of claim 1, wherein the test compound is selected from the group consisting of: a polypeptide, a small molecule, a nucleic acid, an antibody, an antibody fragment, and combinations thereof.

3. The method of claim 1, wherein the albumin polypeptide is a wild type albumin polypeptide.

4. The method of claim 1, wherein the albumin polypeptide or fragment thereof is a human, mouse or rat albumin polypeptide.

5. The method of claim 1, wherein the FcRn polypeptide is a wild type FcRn polypeptide.

6. The method of claim 1, wherein the FcRn polypeptide or fragment thereof is a human FcRn polypeptide.

7. The method of claim 1, wherein either one or both of the FcRn polypeptide or fragment thereof and the albumin polypeptide or fragment thereof are fluorescently labeled.

8. The method of claim 1, further comprising:
selecting a test compound that inhibits binding between the FcRn polypeptide or fragment thereof and the albumin polypeptide or fragment thereof,
administering the test compound to a test animal expressing an FcRn polypeptide or albumin-binding fragment thereof and an albumin polypeptide or FcRn-binding fragment thereof; and
determining a level of the albumin polypeptide or fragment thereof in a body fluid of the test animal;
wherein a change in the level of the albumin polypeptide or fragment thereof in the body fluid of the animal in the presence of the test compound as compared to in the absence of the test compound indicates that the test compound is a candidate compound for decreasing the concentration of an albumin-binding toxin in a subject.

9. The method of claim 8, wherein the body fluid is selected from the group consisting of bile, urine, and feces, and wherein the change in the level of the albumin polypeptide or fragment thereof is an increase in the level in the body fluid.

10. The method of claim 8, wherein the body fluid is blood or lymph, and wherein the change in the level of the albumin polypeptide or fragment thereof is a decrease in the level in the blood or lymph.

11. The method of claim 1, further comprising:
selecting a test compound that inhibits binding between the FcRn polypeptide or fragment thereof and the albumin polypeptide or fragment thereof,
administering the test compound and an albumin-binding toxin to a test animal expressing an FcRn polypeptide or albumin-binding fragment thereof and an albumin polypeptide or FcRn-binding fragment thereof; and
determining an effect of the albumin-binding toxin in the test animal; wherein a change in the effect of the albumin-binding toxin in the presence of the test compound as compared to in the absence of the test compound indicates that the test compound is a candidate compound for decreasing the concentration of the albumin-binding toxin in a subject.

12. The method of claim 8, wherein the test animal expresses a human FcRn polypeptide or a fragment thereof.

13. The method of claim 8, wherein the test animal expresses a human albumin polypeptide or a fragment thereof.

14. A method of reducing levels of an albumin-binding toxin in a subject, the method comprising administering to the subject a therapeutically effective amount of an antibody or antigen-binding portion thereof that binds specifically to FcRn and disrupts binding between FcRn and albumin.

15. The method of claim 14, wherein the step of administering is selected from the group consisting of: intravenous administration, intradermal administration, subcutaneous administration, oral administration, transdermal administration, transmucosal administration, rectal administration, and combinations thereof.

16. The method of claim 1, wherein the albumin-binding toxin is selected from the group consisting of copper, hematin, long-chain fatty acid, zinc, bilirubin, thyroxine, eicosanoids, tryptophan, vitamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, quinidine, ricin, and acetaminophen.

17. The method of claim 14, wherein the albumin-binding toxin is selected from the group consisting of copper, hematin, long-chain fatty acid, zinc, bilirubin, thyroxine, eicosanoids, tryptophan, vitamin D3, bile acids, calcium, magnesium, chloride, indomethacin, bromphenol blue, salicylate, warfarin, phenylbutazone, digoxin, furosemide, phenytoin, chlorpropamide, benzylpenicillin, Evans blue, diazepam, ibuprofen, naproxen, clofibrate, chlorpromazine, imipramine, quinidine, ricin, and acetaminophen.

18. The method of claim 11, wherein the test animal expresses a human FcRn polypeptide or a fragment thereof.

19. The method of claim 11, wherein the test animal expresses a human albumin polypeptide or a fragment thereof.

* * * * *

UNITED STATES PATENT AND TRADEMARK OFFICE
CERTIFICATE OF CORRECTION

| | | |
|---|---|---|
| PATENT NO. | : 8,232,067 B2 | Page 1 of 1 |
| APPLICATION NO. | : 13/322983 | |
| DATED | : July 31, 2012 | |
| INVENTOR(S) | : Richard S. Blumberg et al. | |

It is certified that error appears in the above-identified patent and that said Letters Patent is hereby corrected as shown below:

On the Title Page, Col. 2 (Other Publications), Line 13, delete "Distint" and insert -- Distinct --;

In Col. 23, Line 19 (approx.), in Claim 1, delete "thereof" and insert -- thereof; --;

In Col. 23, Line 22 (approx.), in Claim 1, delete "thereof" and insert -- thereof; --;

In Col. 24, Line 42, in Claim 16, delete "bromphenol" and insert -- bromophenol --;

In Col. 24, Line 51, in Claim 17, delete "bromphenol" and insert -- bromophenol --.

Signed and Sealed this
Twenty-third Day of October, 2012

David J. Kappos
*Director of the United States Patent and Trademark Office*